US010263384B2

(12) United States Patent
Cannon et al.

(10) Patent No.: US 10,263,384 B2
(45) Date of Patent: Apr. 16, 2019

(54) LASER SYSTEM HAVING A DUAL PULSE-LENGTH REGIME

(71) Applicant: LUMENIS LTD., Yokneam Ilit (IL)

(72) Inventors: Christopher Cannon, Yokneam Ilit (IL); Idan Aviad, Yokneam Ilit (IL); Yair Manor, Yokneam Ilit (IL); Yehoram Har-Even, Yokneam Ilit (IL); Alon Shacham, Yokneam Ilit (IL); Albert Ben-Shlomo, Yokneam Ilit (IL)

(73) Assignee: Lumenis Ltd. (IL)

( * ) Notice: Subject to any disclaimer, the term of this patent is extended or adjusted under 35 U.S.C. 154(b) by 0 days.

(21) Appl. No.: 15/783,019

(22) Filed: Oct. 13, 2017

(65) Prior Publication Data
US 2018/0109066 A1 Apr. 19, 2018

Related U.S. Application Data

(60) Provisional application No. 62/408,107, filed on Oct. 14, 2016.

(51) Int. Cl.
*H01S 3/13* (2006.01)
*H01S 3/091* (2006.01)
(Continued)

(52) U.S. Cl.
CPC .......... *H01S 3/0912* (2013.01); *H01S 3/1024* (2013.01); *H01S 3/1305* (2013.01);
(Continued)

(58) Field of Classification Search
CPC .... H01S 3/1024; H01S 3/1305; H01S 3/1306; H01S 3/1312
See application file for complete search history.

(56) References Cited

U.S. PATENT DOCUMENTS 6,377,594 B1 4/2002 Miller
6,829,259 B2 * 12/2004 Pontis ..................... H01S 5/141
372/20
(Continued)

FOREIGN PATENT DOCUMENTS

WO 2006091714 8/2006

OTHER PUBLICATIONS

Search Report and Written Opinion—Corresponding PCT Application No. PCT/IL2017/051138, dated Dec. 27, 2017, 7 pages.

*Primary Examiner* — Michael Carter
(74) *Attorney, Agent, or Firm* — ISUS Intellectual Property; A. Jason Mirabito

(57) ABSTRACT

A single loop hardware-based system for producing laser pulses in a microsecond scale operational mode includes a GUI to enable a user to select the operational mode of the system; a laser source for producing one or more laser beam pulses, the laser source being a diode laser pump source module; a DSP which enables and disables a hardware-based FPGA. The FPGA controls the diode pump source module. When a user selects one or more microsecond scale laser sub-pulses on the GUI, the DSP transmits to the FPGA the sub-pulse energy level and the sub-pulse on-time selected by the user on the GUI. A photodetector operatively connected to the hardware-based system measures the power of the laser pulse beam that was transmitted to the photodetector and, in a feedback mode, transmits a feedback signal of that power measurement to the FPGA. The FPGA compares the power of the laser beam measured by the photodetector to the power of the laser beam selected by the user on the GUI. If the power level read by the FPGA is higher than the selected power level, the FGPA decreases the power level to the pumping source module for any subsequent laser pulses; and if the power level read by the FPGA is less than the
(Continued)

selected power level, the FGPA increases the power level to the pumping source module for subsequent laser pulses.

17 Claims, 15 Drawing Sheets

(51) Int. Cl.
| | |
|---|---|
| *H01S 3/102* | (2006.01) |
| *H01S 3/131* | (2006.01) |
| *G06F 3/0484* | (2013.01) |
| *H01S 3/094* | (2006.01) |
| *H01S 3/0941* | (2006.01) |
| *H01S 3/081* | (2006.01) |
| *H01S 3/109* | (2006.01) |
| *H01S 3/06* | (2006.01) |
| *H01S 3/10* | (2006.01) |

(52) U.S. Cl.
CPC ........ *H01S 3/1312* (2013.01); *G06F 3/04842* (2013.01); *H01S 3/0602* (2013.01); *H01S 3/0815* (2013.01); *H01S 3/0941* (2013.01); *H01S 3/09415* (2013.01); *H01S 3/094076* (2013.01); *H01S 3/109* (2013.01); *H01S 3/10069* (2013.01); *H01S 3/1306* (2013.01)

(56) References Cited

U.S. PATENT DOCUMENTS

| | | | |
|---|---|---|---|
| 7,771,417 B2* | 8/2010 | Telfair | A61F 9/008 372/22 |
| 2004/0213306 A1* | 10/2004 | Fennema | H01S 5/141 372/38.01 |
| 2008/0276192 A1* | 11/2008 | Jones | A61C 1/0015 715/772 |

* cited by examiner

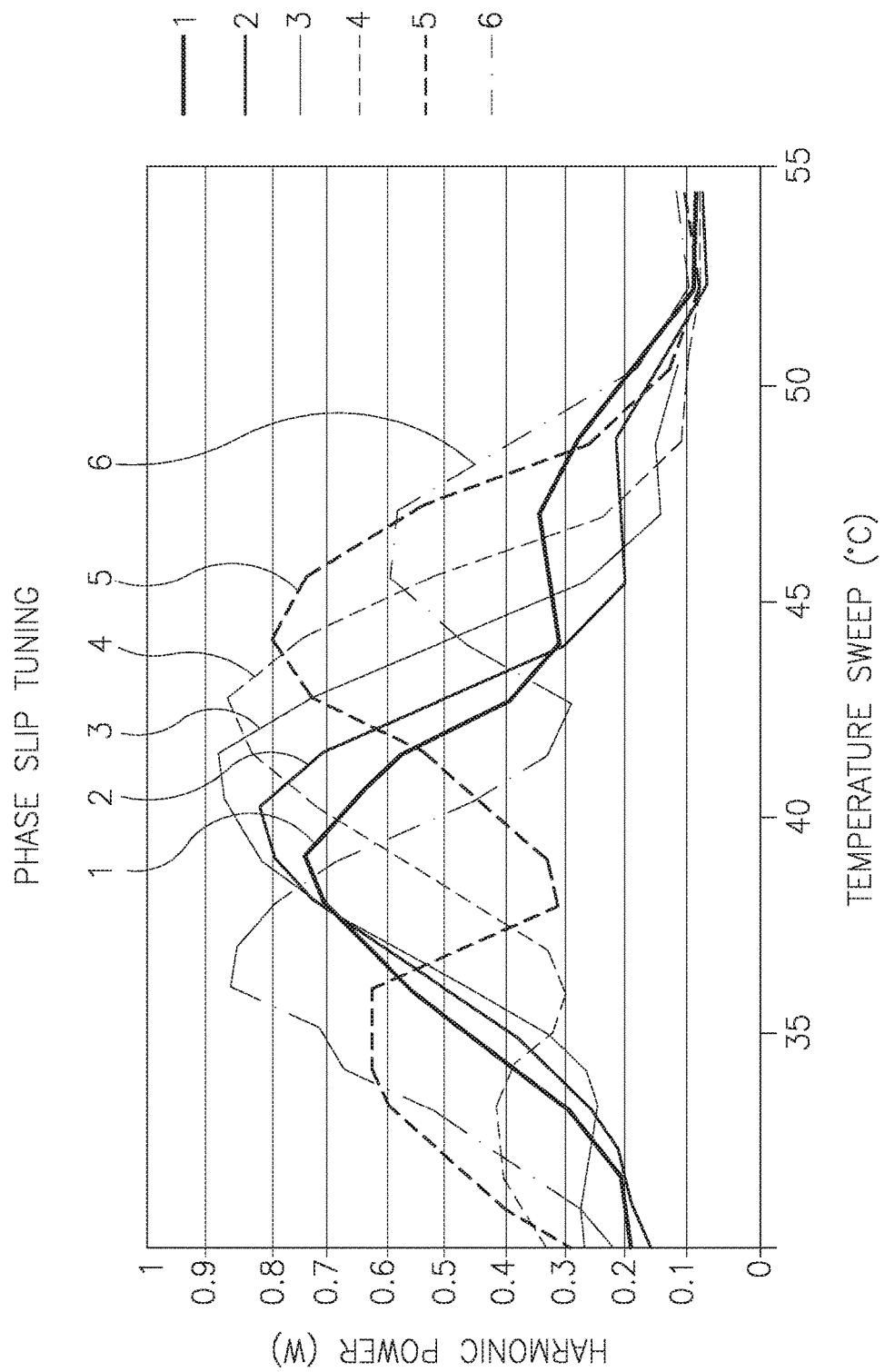

LASER SYSTEM HAVING A DUAL PULSE-LENGTH REGIME

RELATED APPLICATIONS

This application is related to and claims priority to U.S. Provisional Application Ser. No. 62/408,107, filed Oct. 14, 2016, the entirety of which is herein incorporated by reference.

BACKGROUND OF THE PRESENT INVENTION

Various eye diseases may be treated by various laser treatments. In some of these treatments, such as with laser photocoagulation, there is a visible end point for the treatment e.g. retinal blanching. Subthreshold laser treatment such as selective laser trabeculoplasty described in U.S. Pat. No. 5,549,596 discloses a short pulse laser treatment delivered to the trabecular meshwork providing no visible end point for the treatment. The '596 patent teaches laser pulse durations shorter than the thermal relaxation time of a target tissue in order to confine thermal damage in the target tissue only and to avoid collateral thermal damage. The thermal relaxation time of a particle is related to the particle size. In the case of melanin granules within pigmented trabecular meshwork cells selective cell killing may be achieved with a 532 nm laser at pulse durations of 10 nanoseconds.

Roider teaches ("Microphotocuagulation: Selective Effects of Repetitive Short Laser Pulses"; Vol. 90 pp. 8643-8647, September 1993; Medical Sciences) targeting single RPE cell layer while sparing neural retina by using microseconds laser pulses which are again shorter than the thermal relaxation time of the target tissue. Roider teaches chopping a continuous Argon laser producing 514 nm into microseconds pulses using an acousto-optical modulator. Moreover, in order to avoid negative effects associated with strong local temperature gradient such as cavitation or hemorrhage, Roider teaches inducing additive tissue damage by repetitive short subthreshold pulses, each too small in energy to cause tissue damage by itself. Before a next laser pulse is delivered, heat dissipates to surrounding tissue and the target tissue cools. The heat dissipation out of the target tissue after each laser pulse leads to only a nonsignificant average temperature increase inside adjacent tissue.

Lanzzeta teaches the clinical effectiveness of Non Ophthalmoscopically Visible Photocoagulation (NOVEP). ("Theoretical Bases of Non-Ophthalmoscopically Visible Endpoint Photocoagulation"; Seminars in Ophthalmology; 2001; Vol. 16, No. 1, pp. 8-11). According to Lanzzeta, the target is to raise the temperature of the RPE just to, and without exceeding, the protein-denaturation-threshold. A resulting thermal wave to adjacent tissue will be spread and will reach the neural retina however at a temperature bellow the protein-denaturation-threshold causing no damage however leaving no clinically visible endpoint. Lanzzeta further teaches that a repetitive series of pulses may replace a single pulse using the N-1/4 law for suprathreshold treatment or to be decreased by a factor of 4-10 for a subthreshold treatment. Moreover, Lanzzeta teaches minimizing thermal additivity by not only controlling the pulse "ON" duration, the pulse energy and the peak power, but also by controlling the "OFF" times and duty cycle per second (Hz) so that the temperature rise of the target tissue caused by each pulse is allowed to return to baseline before the arrival of the next pulse.

In order to control the regime of pulses as described above, the '596 patent teaches "a control unit configured to control the irradiating of the tissue with the one or more radiation pulses such that the total radiation energy applied to the tissue provides a sub lethal fluence to the pigmented target cells, thereby selectively photostimulating pigmented cells in the tissue".

U.S. Pat. No. 7,115,120 also teaches "control over the laser dosimetry to ensure that laser energy reaches the threshold required for RPE cell killing (a therapeutic endpoint), but avoids the administration of laser energies sufficient to damage adjacent cells, such as photoreceptors (collateral damage control)".

U.S. Pat. No. 5,805,622 discloses an expensive control system for a medical laser which is configured to produce microsecond pulses. The control system requires a very fast feedback loop and several kV which must be applied to a Pockels cell in order to dampen spikes in the laser pulse.

Also known in the prior art for ophthalmological green lasers are fast photodetectors which are configured to sense the output power level of the laser and a software control light loop working on the millisecond scale. A hardware control loop, which is based on the fast photodetector, is designed to provide spike safety protection against high power light spikes.

U.S. Pat. No. 7,771,417 teaches a medical laser which is also configured to deliver microseconds pulses of green laser to provide subthreshold treatment. The '417 patent describes a control system having a two control loops—a first, slow, software light control loop in the millisecond regime and a second, fast, hardware light control loop in the microsecond regime.

It is therefore one aspect of the present invention to provide a simpler control system for a medical green laser which is configured to deliver laser pulses in the microseconds scale.

SUMMARY OF THE PRESENT INVENTION

In an aspect, a single loop hardware-based system for producing laser pulses in a microsecond scale operational mode includes a GUI to enable a user to select the operational mode of the system; a laser source for producing one or more laser beam pulses, the laser source being a diode laser pump source module; a DSP which enables and disables a hardware-based FPGA. The FPGA controls the diode pump source module. When a user selects one or more microsecond scale laser sub-pulses on the GUI, the DSP transmits to the FPGA the sub-pulse energy level and the sub-pulse on-time selected by the user on the GUI. A photodetector operatively connected to the hardware-based system measures the power of the laser pulse beam that was transmitted to the photodetector and, in a feedback mode, transmits a feedback signal of that power measurement to the FPGA; and wherein the FPGA compares the power of the laser beam measured by the photodetector to the power of the laser beam selected by the user on the GUI. If the power level read by the FPGA is higher than the selected power level, the FGPA decreases the power level to the pumping source module for any subsequent laser pulses; and if the power level read by the FPGA is less than the selected power level, the FGPA increases the power level to the pumping source module for subsequent laser pulses.

In another aspect, a beam splitter is provided in the optical path of the diode laser pump source module, the beam splitter dividing a laser pulse from the laser source into two portions; one portion of the laser beam pulse being transmitted to a target tissue; the other portion of the laser beam pulse being transmitted to a photodetector. The FPGA reads the feedback signal once every one to ten microseconds to compare measured power to selected power. The GUI controls the system to deliver one pulse or more than one pulse in the microsecond operational mode. The beam splitter is one of a: mirror or a prism.

In a further aspect, the photodetector comprises more than one photodetector for redundancy operation.

In yet another aspect, the system further includes a calibration device to calibrate the power of one or more pulses in the microsecond scale of operation.

In yet a further aspect, when a user sets on the GUI the desired pulse power level, the FGPA causes the laser module to provide one or more pulses to be measured by the photodetector to determine whether the set desired pulse level is reached; and, if so, the set power level is stored in a memory of a computer system.

In an aspect, the calibration device calibrates using a two-step algorithm to stabilize the energy profile of the microsecond operational mode, wherein the algorithm includes a sequence of: a first energy step of a set energy value, followed by a first delay period, then a second energy step of a set value followed by a second delay period. After the second delay, the FGPA samples the photodetector at a specified rate of frequency in the microsecond operational mode to compare the sampled measurement from the photodetector to the selected energy level.

In an aspect, a method for producing laser pulses with a single loop hardware-based system includes the steps of: providing a single loop hardware-based system capable of producing laser pulses in a microsecond scale operational mode, the system including: a GUI to enable a user to select the operational mode of the system; a laser source for producing one or more laser beam pulses, the laser source being a diode laser pump source module; a DSP which enables and disables a hardware-based FPGA; the diode pump source module being controlled by the FGPA. The method includes: when a user selects one or more microsecond scale laser sub-pulses on the GUI, the DSP transmits to the FPGA the sub-pulse energy level and the sub-pulse on-time selected by the user on the GUI. A photodetector is operatively connected to the hardware-based system to measure the power of the laser pulse beam that was transmitted to the photodetector and, in a feedback mode, transmits a feedback signal of that power measurement to the FPGA; the FPGA compares the power of the laser beam measured by the photodetector to the power of the laser beam selected by the user on the GUI. Further, if power level read by the FPGA is higher than the selected power level, the FGPA decreases the power level to the pumping source module for any subsequent laser pulses; and if the power level read by the FPGA is less than the selected power level, the FGPA increases the power level to the pumping source module for subsequent laser pulses.

In a further aspect, the method further includes the step that when a user sets on the GUI the desired pulse power level, the FGPA causes the laser module to provide one or more pulses to be measured by the photodetector to determine whether the set desired pulse level is reached; and, if so, the set power level is stored in a memory of a computer system. A calibration device calibrates using a two-step algorithm to stabilize the energy profile of the microsecond operational mode. The algorithm includes a sequence of: a first energy step of a set energy value, followed by a first delay period, then a second energy step of a set value followed by a second delay period. The method includes the further step wherein, after the second delay, the FGPA sampling the photodetector at a high rate of frequency in the microsecond operational mode and comparing the sampled measurement from the photodetector to the selected energy level.

BRIEF DESCRIPTION OF THE DRAWINGS

FIGS. 14 and 15 illustrate a phase slip schematic and phase slip tuning diagram in accordance with the present invention.

DETAILED DESCRIPTION OF THE PRESENT INVENTION

Figure 9:
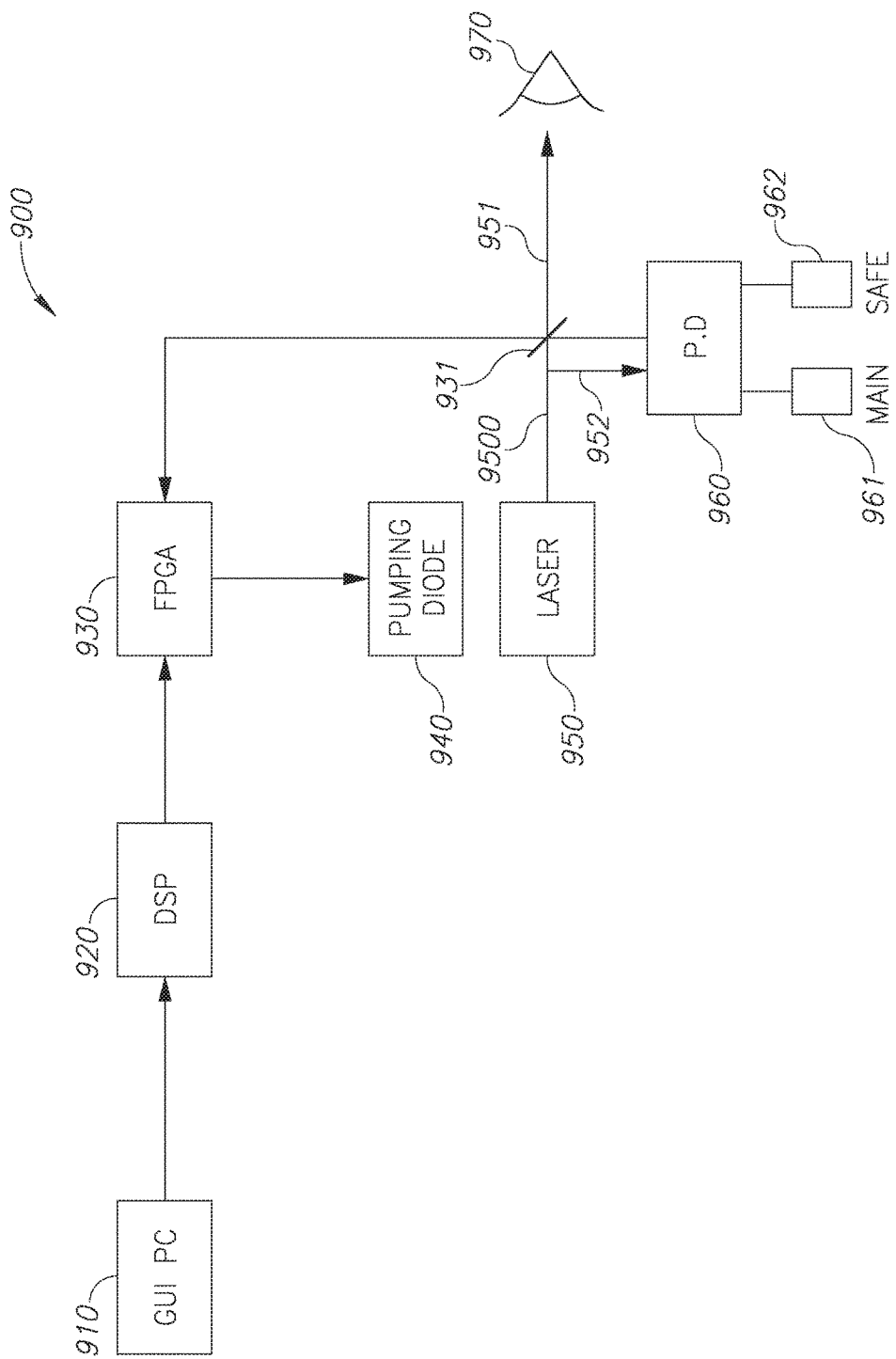
FIG. 9 is a schematic illustrating the structure of components of the present invention.

The apparatus of the present invention will be described below in connection with the schematic diagram of FIG. 9. In that figure, reference numeral 910 relates to the human interface into the system, and is marked as a GUI (for Graphical User Interface). The operation of the present invention will now be described in connection with what appears on such GUI.

Figure 1:
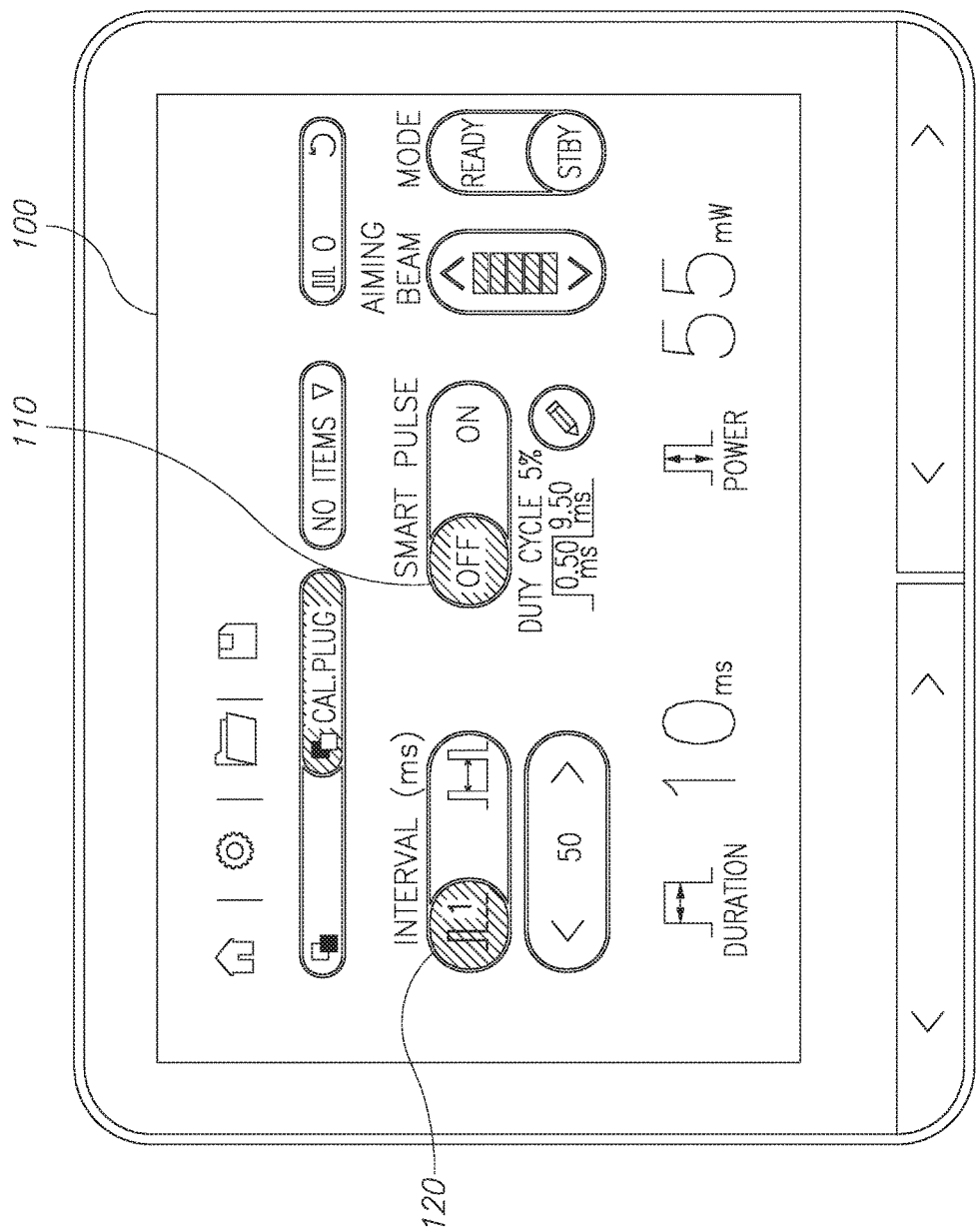
FIGS. 1, 2, 3, 5, and 7 are screen shots showing a GUI in the operation of the present invention.

FIG. 1 shows a screen shot 100 that appears on the GUI of a laser system of the present invention. The laser system is configured to deliver in a first state, laser pulses having a duration on the scale of milliseconds for providing suprathreshold treatments. The laser system is also configured to deliver in a second state, laser pulses having a duration on the scale of microseconds for providing subthreshold treatments. When button 110 is in Off position the system is configured to operate in the first state and when button 110 is in On position the system is configured to operate in the second state.

Figure 2:
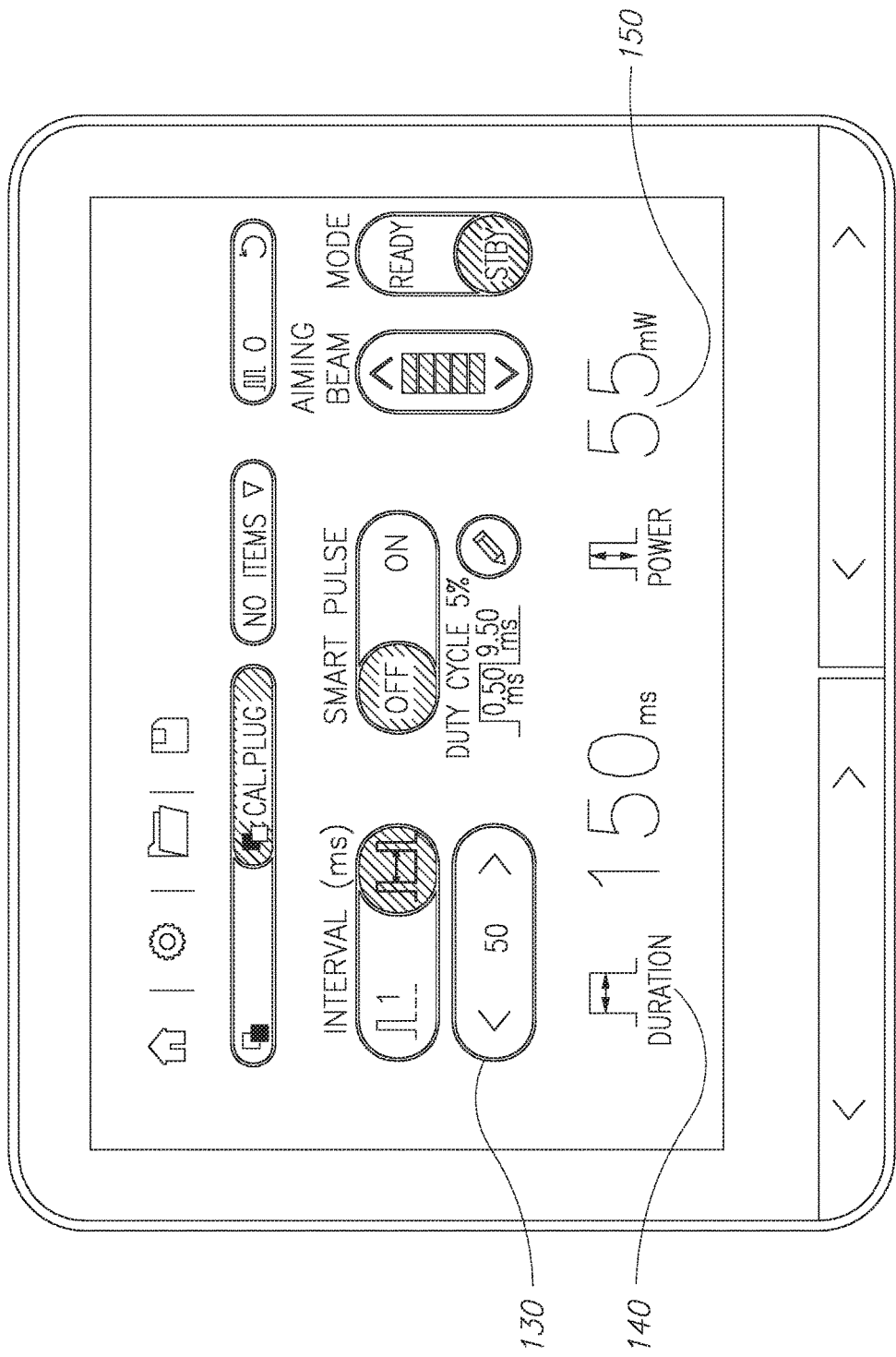

In the first state, button 120 is configured to switch the system from single pulse mode into a repeat mode. In a single pulse mode, each activation of the system (such as by a footswitch) will cause the laser system to shoot a single pulse. In a repeat mode, as long as the activating mechanism is turned on, e.g., as long as the footswitch is pressed, the system will continue to generate repeated pulses. The time delay between consecutive pulses, the pulse-off time, can be selected by a user through button 130 shown in FIG. 2. Pulse duration 140, which is the pulse on-time, and energy level per pulse 150 may also be selected by a user.

Figure 3:
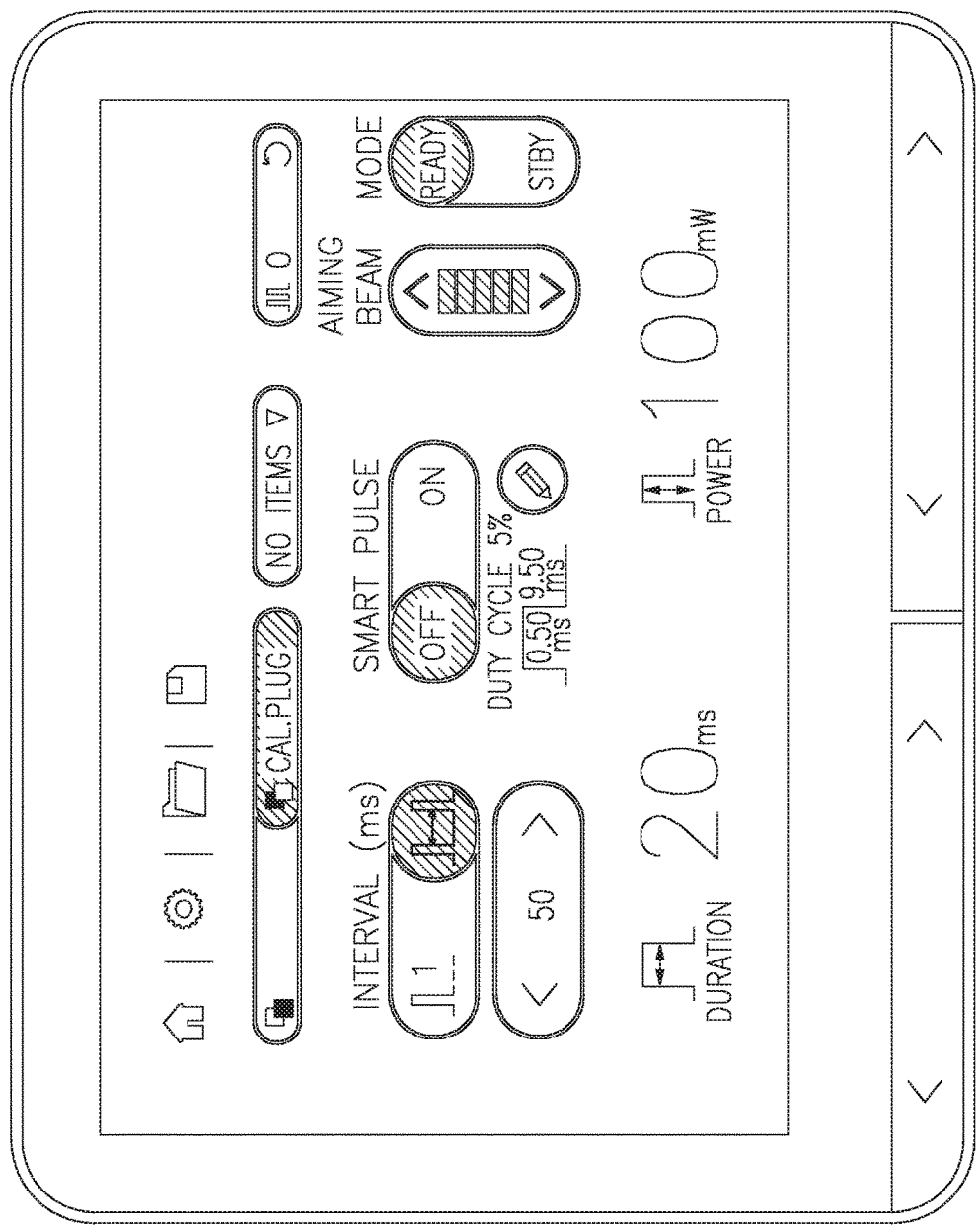

FIG. 3 shows the laser system in a first state in a repeat mode which is selected to deliver a sequence of pulses every 50 milliseconds, each pulse is configured to deliver 100 mW through a pulse on-time of 20 milliseconds. A control system which will be described below turns the laser system on when a pulse starts and turns it off at the end of a pulse.

Figure 4:
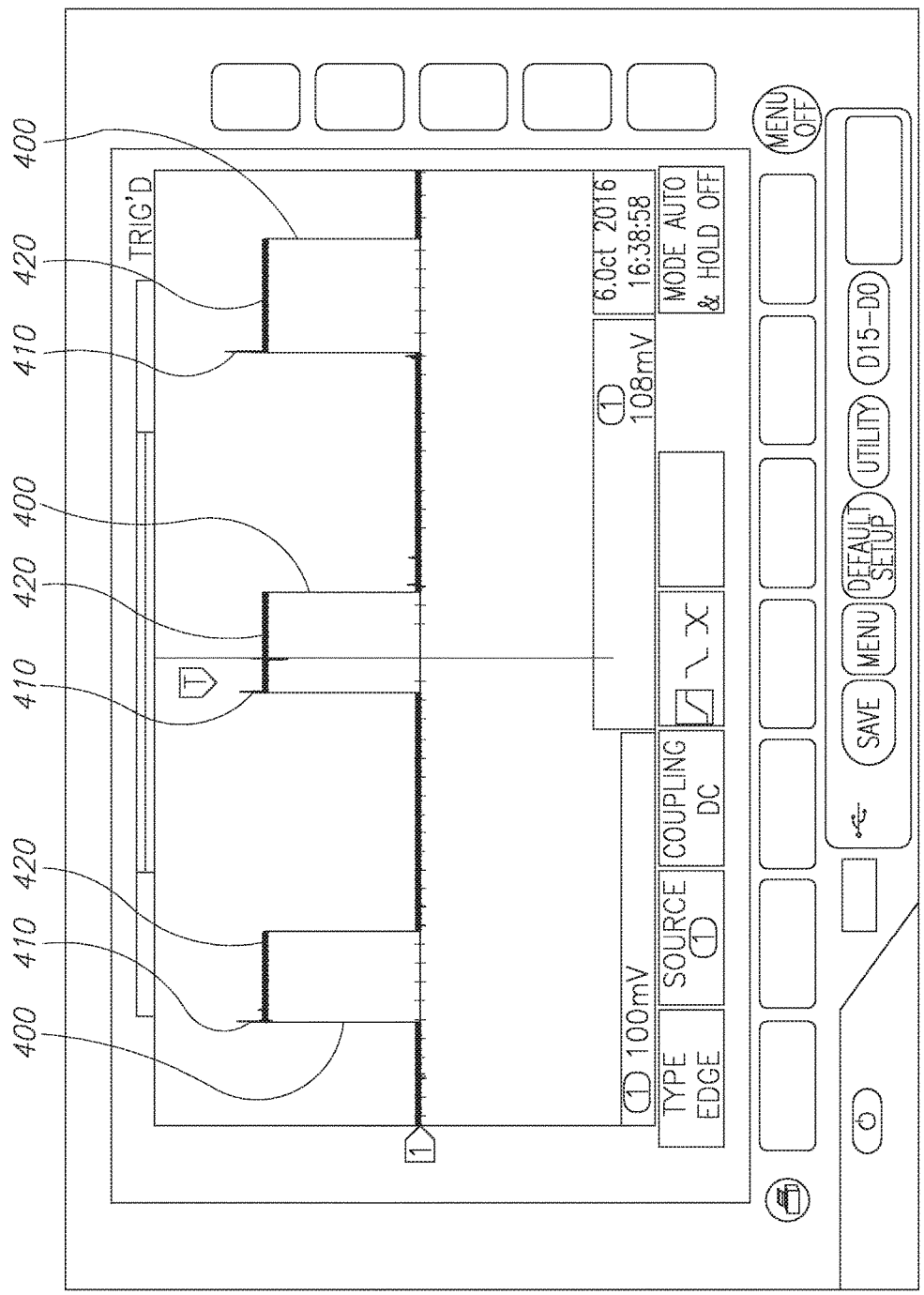
FIGS. 4, 6 and 8 are oscilloscope screen shots showing the operation of the present invention.

As can be seen in FIG. 4 shown on an oscilloscope, in the above-mentioned example of a 20 millisecond pulse on-time, each pulse 400 is characterized by spikes 410 at the beginning of pulse 400 followed by a relatively flat zone 420. Raised energy spikes associated with the activation of a laser system are known and are a result of multiple optical and electrical parameters associated with the laser. As can be seen in FIG. 4, the relative percentage of spikes 410 in a relatively long pulse in the millisecond scale is almost negligible and hardly changes the energy average of the pulses 400.

Figure 5:
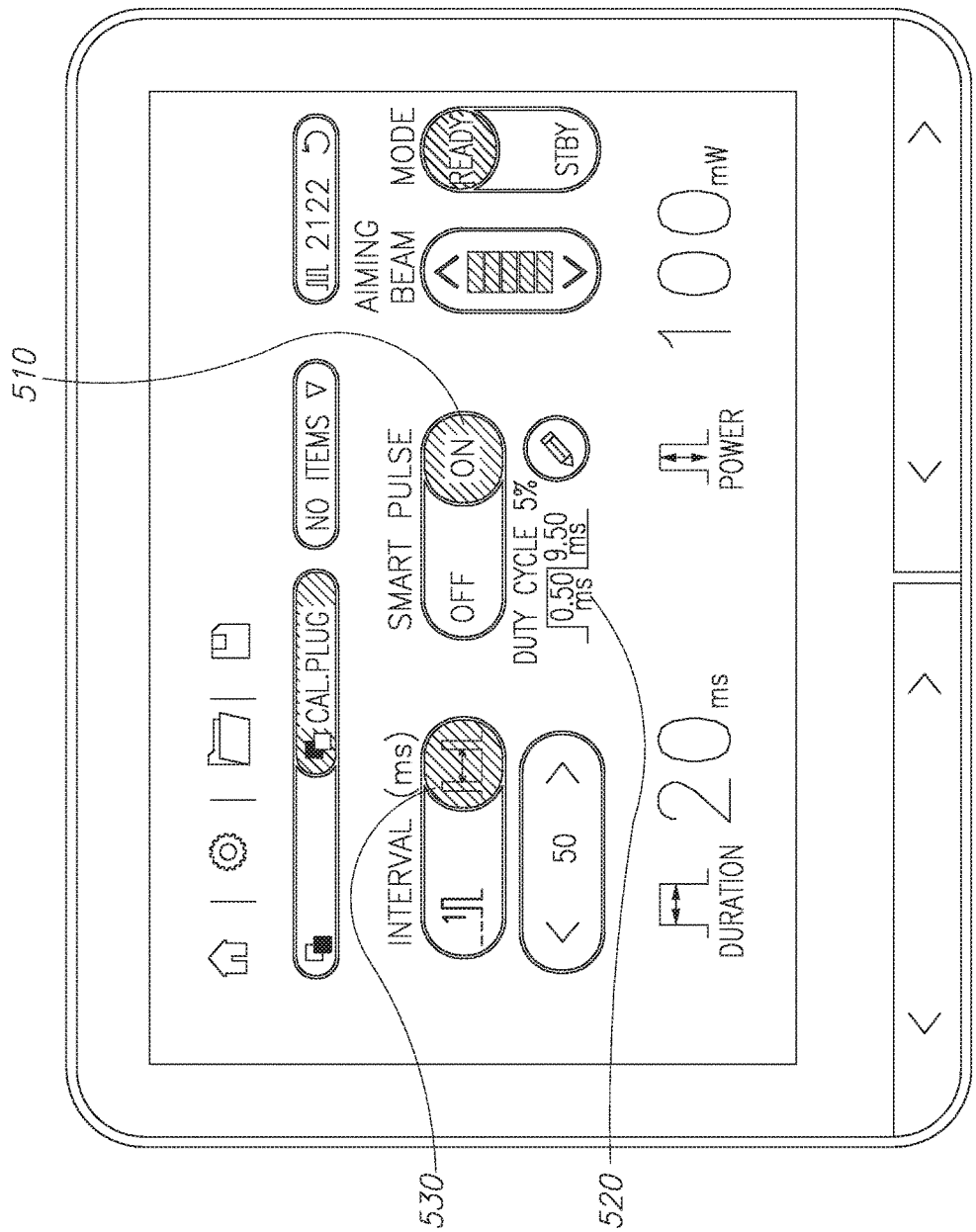

FIG. 5 shows the laser system in the second state. Button 510 here has been switched on and this has switched the laser system to operate on a microseconds laser pulse scale. In this second state, the laser system is configured to deliver a train of sub-pulses each having a corresponding sub-pulse on time and sub-pulse off time as indicated in area 520. Duty cycles are calculated by the ratio of (sub-pulse on time) over the (sub-pulse on time+sub-pulse off time) and is provided in percentage representation. In this example in FIG. 5, the duty cycle is seen to be 5%. The laser system is configured to allow a user to select a sub-pulse on time and duty cycle and based on that the system calculates the corresponding sub-pulse off time.

In the example of FIG. 5, a sub-pulse on time of 0.5 millisecond (500 microsecond) was chosen with a duty cycle of 5%. The corresponding sub-pulse off time calculated by the laser system is 9.5 millisecond. Further, FIG. 5 shows that the system is configured to deliver a train of sub-pulses for a period of 20 milliseconds, duration, and that each sub-pulse is configured to deliver 100 mW. Since the laser system is also in a repeat mode as indicated by the position of button 530, the same train of pulses mentioned above will be delivered repeatedly by the laser system as long as it is activated with off times between one train of pulses to the next train of pulses, of 50 milliseconds.

Figure 6:
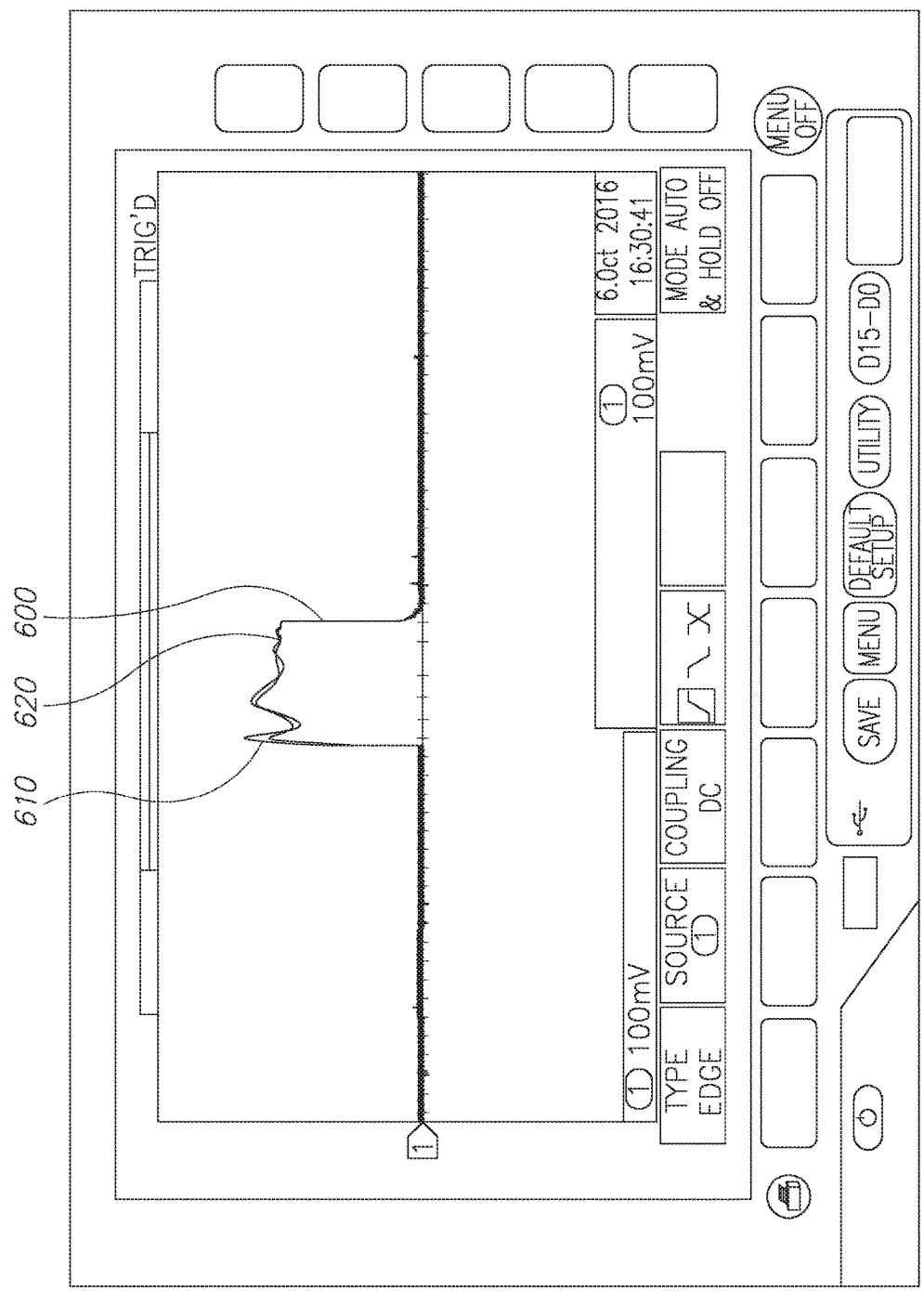

The oscilloscope image in FIG. 6 shows a pulse 600 of 500 microseconds per the above-mentioned settings having an unstable area 610 and a more stable area 620. As can be seen, in the case of a microsecond pulse scale, energy fluctuations associated with the rise time of pulse 600 consumes significant time of the entire pulse and therefore influences dramatically the energy profile reaching a target tissue.

Figure 7:
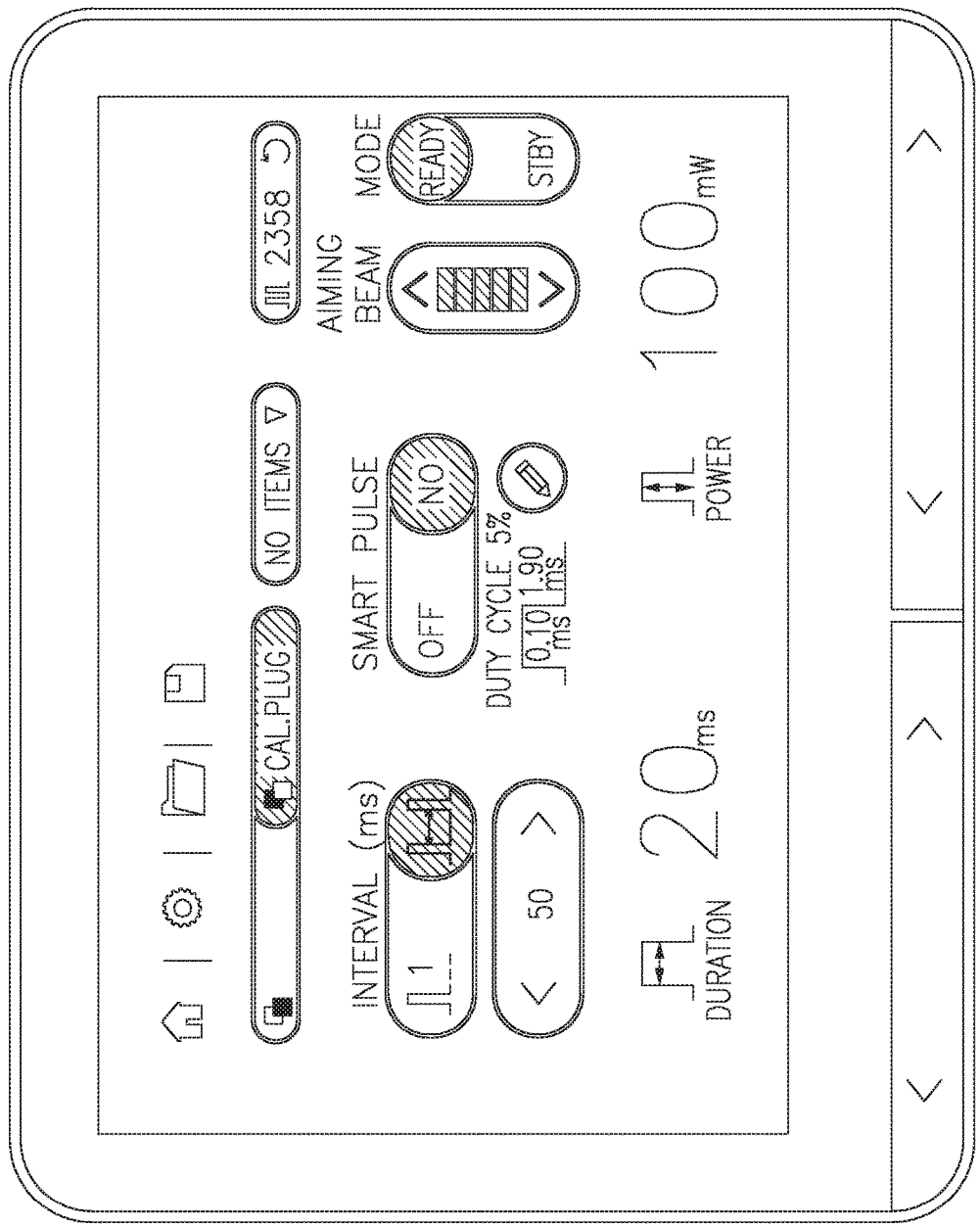
Figure 8:
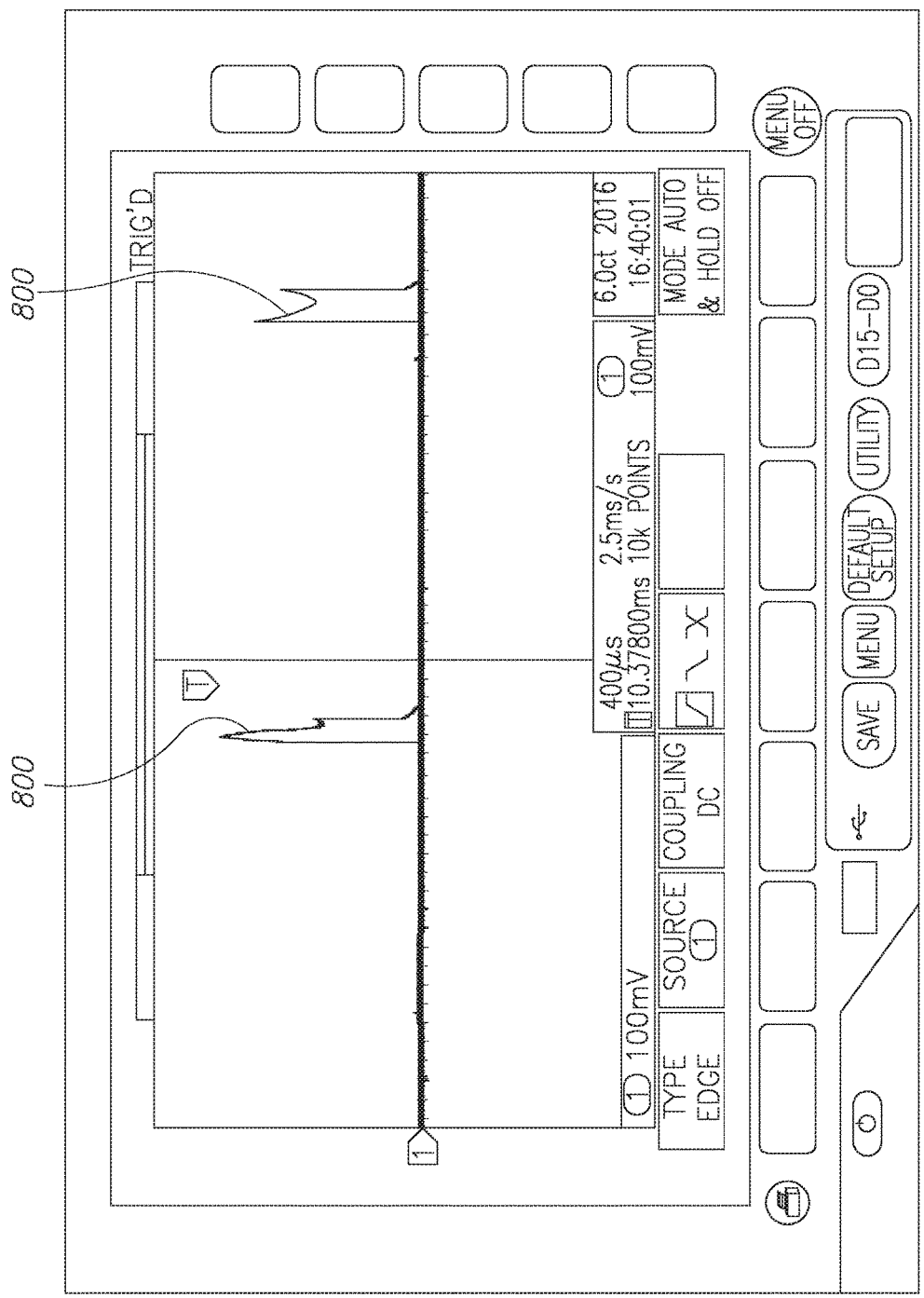

FIG. 7 shows a laser system in the second state which is configured to deliver a train of sub-pulses having sub-pulse on time of 100 microsecond. Such sub-pulses are shown on the oscilloscope image of FIG. 8 as pulses 800. As can be seen, due to the short pulse, the entire pulse profile is characterized by strong energy fluctuations.

It is one aspect of the present invention to reduce these fluctuations by providing a better control system and method as described below. Referring now to FIG. 9, this figure shows a general schematic of a laser system 900. According to this aspect of the invention, a GUI module 910 provides features such as described above in reference to FIGS. 1-8. A computer system having a processor and a memory may be operatively associated with the GUI module 910. DSP module 920 is configured to enable and disable FPGA module 930. FPGA module 930 is a single hardware control loop which controls pumping diode module 940 which is configured to pump laser 950. Laser beam 9500 is split by a suitable device such as a prism or mirror setup 931 into a treatment laser beam 951 which is configured to reach target tissue 970 and a feedback laser beam 952 which is configured to be detected by photodetector module 960. For safety reasons, photodetector module has a first main photodetector 961 and a second redundancy photodetector 962. FPGA 930 is configured to receive input signals from the photodetector unit 960. Such signals provide an indication of the intensity of feedback laser beam 952 which can be converted by the FPGA into power values of treatment laser beam 951. In the first state of the laser system which is configured to deliver millisecond pulse scale, DSP 920 is configured to transfer to FPGA 930 the pulse energy level and the pulse on-time selected by a user. If the system is in a repeat mode, DSP 920 also transfers to FPGA 930 the time delay between consecutive pulses as selected by a user.

In the second state of the laser system which is configured to deliver trains of microsecond sub-pulses, DSP 920 is configured to transfer to FPGA 930 the sub-pulse energy level and the sub-pulse on-time selected by a user. If the system is in a repeat mode, DSP 920 also transfers to FPGA 930 the time delay between consecutive trains of sub-pulses as selected by a user. During laser operation, whether in the first or second state, once DSP 920 enables FPGA 930, FPGA turns on pumping diode 940 to activate laser 950 and to irradiate laser beam 9500. A feedback signal is delivered from photodiode module 960 to FPGA 930. FPGA module 930 reads such feedback signal once every 1 microsecond to compare measured power to the power selected by a user. If the power level read by FPGA 930 is higher than the power level selected by the user, FPGA 930 decreases the current level to pumping diode 940. If the power level read by FPGA 930 is lower than the power level selected by the user, FPGA 930 increases the current level to pumping diode 940.

Figure 10:
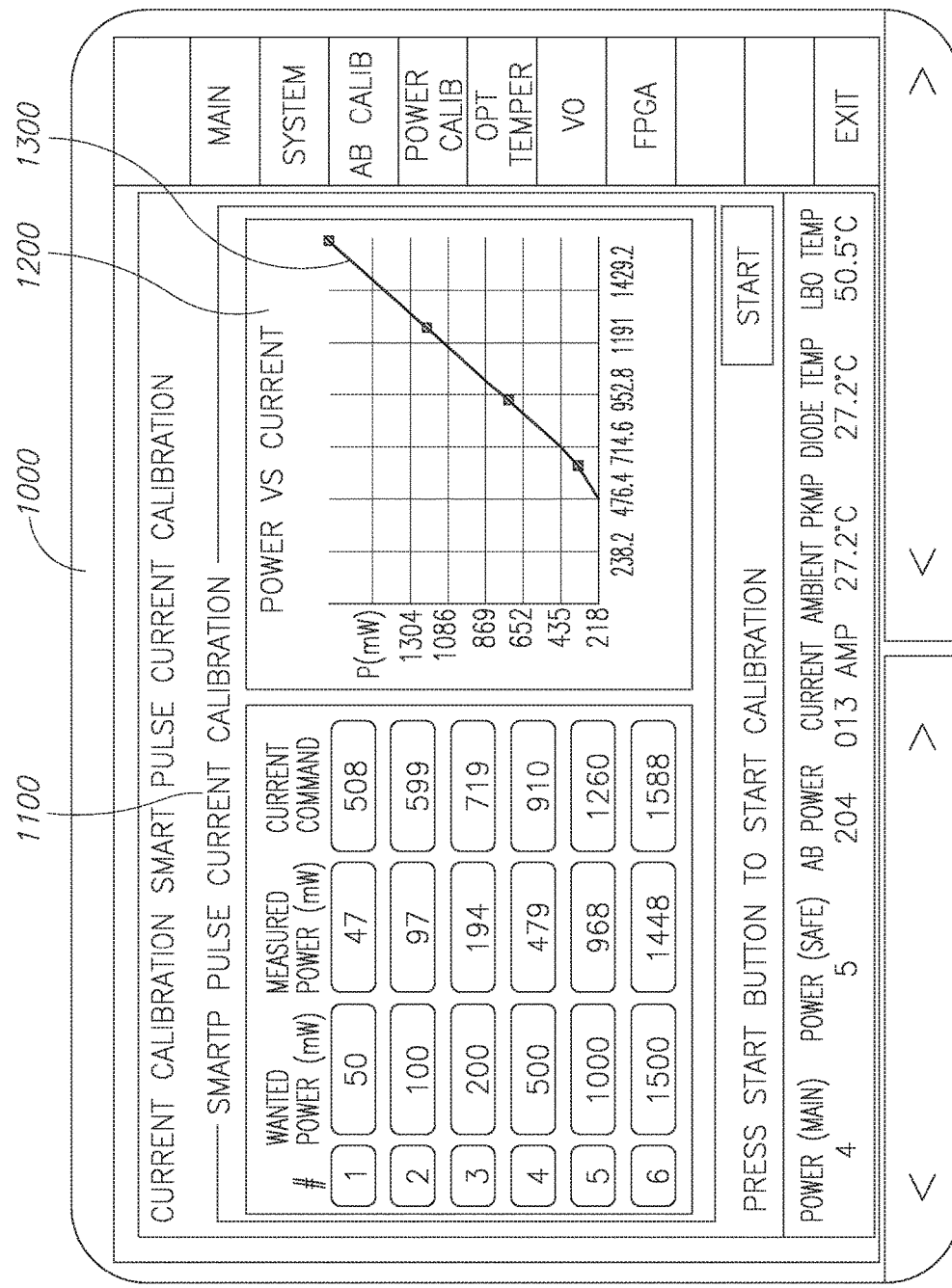
FIGS. 10, 11A-11C, 12 and 13A and 13B show a screenshot and graphical representation of calibration techniques of the present invention.

Referring now to FIG. 10, shown is an example of a current calibration table 1100 for a laser system 1000 as generated in the factory or during service in the field, which is configured to operate in the second, microsecond sub-pulse state. A similar current calibration table, having different numerical values of course, which is configured to operate the laser in a first millisecond state, is also generated in a similar mechanism as will be described below and for simplicity is not shown and duplicated.

The purpose of the calibration process is to search for electrical current values ("DAC" values) to be delivered by FPGA 930 to pumping diode module 940 which correspond to specific optical output power of laser 950. During the calibration process, laser system 1000 is configured to shoot a long series of short pulses. For example, such short pulses may be 50 microsecond pulses or 100 microsecond pulses. According to one example, in order to calibrate laser system 1000 to produce optical output power of about 50 mW, laser system 1000 will measure the electrical current DAC value which provides measured optical power of about 50 mW and store it in row no. 1 as seen in calibration table 1100. In this example, the measure DAC value is shown as 508. Then the system will step to find the DAC value corresponding to a second optical power. In this example, the second step was chosen to be 100 mW. As shown in row no. 2 of calibration table 1100, DAC value 599, for this specific laser system 1000, provides optical power output of 97 mW which is close to and about 100 mW. In a similar way, according to this specific example, laser system 1000 will search for DAC values which provide 200 mW, 500 mW, 1000 mW and 1500 mW. Those values were found to be 719, 910, 1260 and 1588 respectively.

It should be mentioned that other energy steps can be chosen to calibrate laser system 1000. Once calibrated, calibration table 1100 is stored in the computer system. According to one aspect of the invention, a two-step algorithm may be provided for operating the laser. The two-step algorithm has been found to be effective in stabilizing the energy profile of short microsecond pulses which tend to fluctuate as mentioned in the above discussion of FIGS. 6 and 8. According to this aspect of the invention, the hardware control loop of FPGA 930 is configured to send pumping diode 940 a two-step signal.

Figure 12:
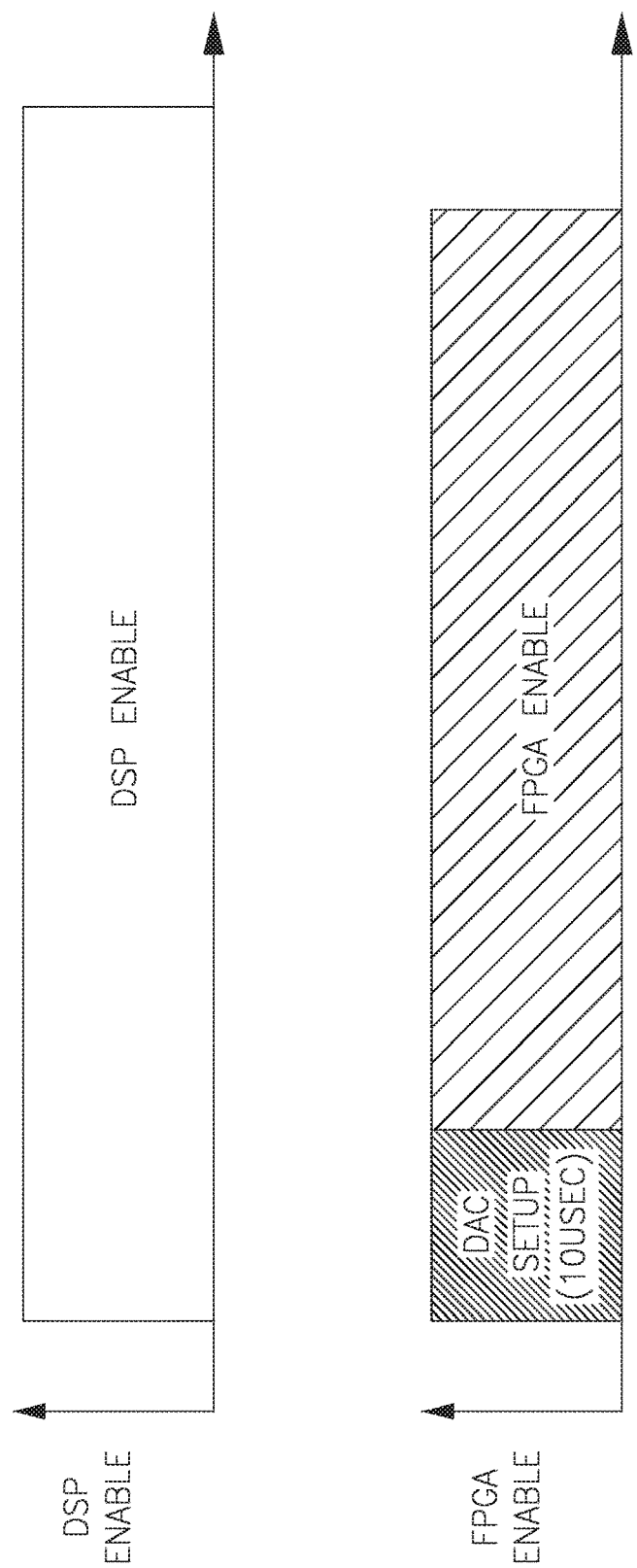

As shown in FIG. 12, once the DSP 920 enables FPGA 930 there is an initial DAC set up period of about 10 microseconds. According to another embodiment of the present invention, DAC set up period may be anywhere between 0 to 30 microseconds. During the DAC set up period, FPGA 930 is set to deliver a first energy step to pumping diode 940. According to one embodiment of the invention, such a first energy step may be 50 mW. According to another embodiment such a first energy step may be anywhere between 50 mW and 150 mW.

Figure 11A:
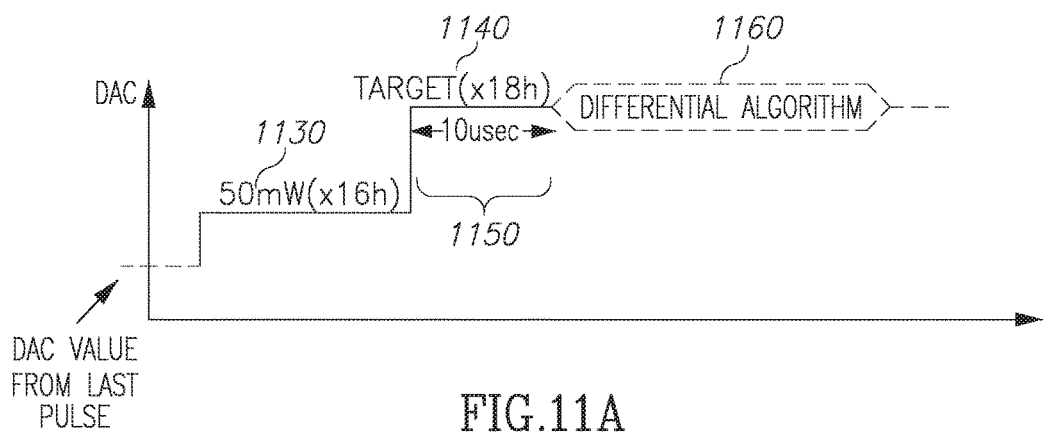
Figure 11B:
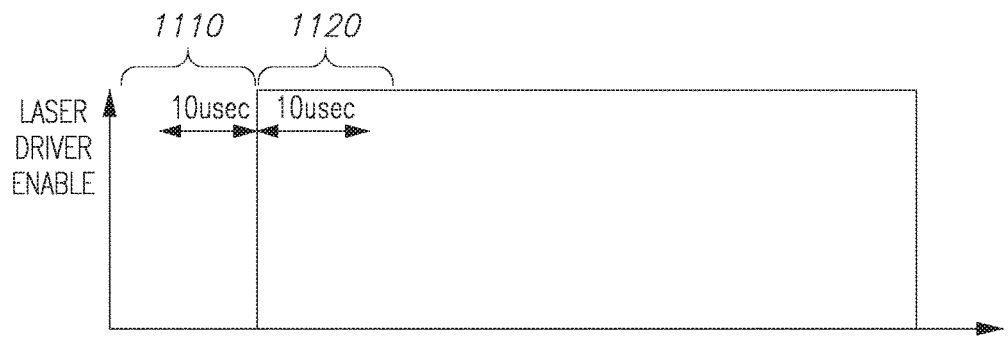
Figure 11C:
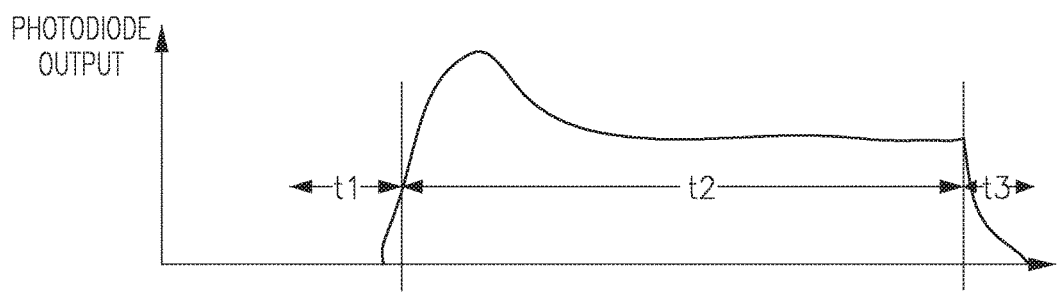

Referring now to FIG. 11, the DAC set up period can be seen as 1110 in FIG. 11*b* and first energy step 1130 is seen in FIG. 11*a*. A second energy step 1140 with another DAC value is triggered by FPGA 930 after a first delay period 1120. The DAC value of second energy step 1140 is calculated and extrapolated based on calibration table 1100 and lies along line 1300 of graph 1200 in FIG. 10 and is correlated to the selected energy level as was selected by the user. After a second delay period 1150, FPGA 930 starts to sample the photodetector at a high frequency, such as once every 1-10 microseconds. In a differential algorithm period 1160, following the second delay period 1150, FPGA 930 compares each sampled measurement of the photodetector to a selected energy power which was selected by a user.

Figure 13A:
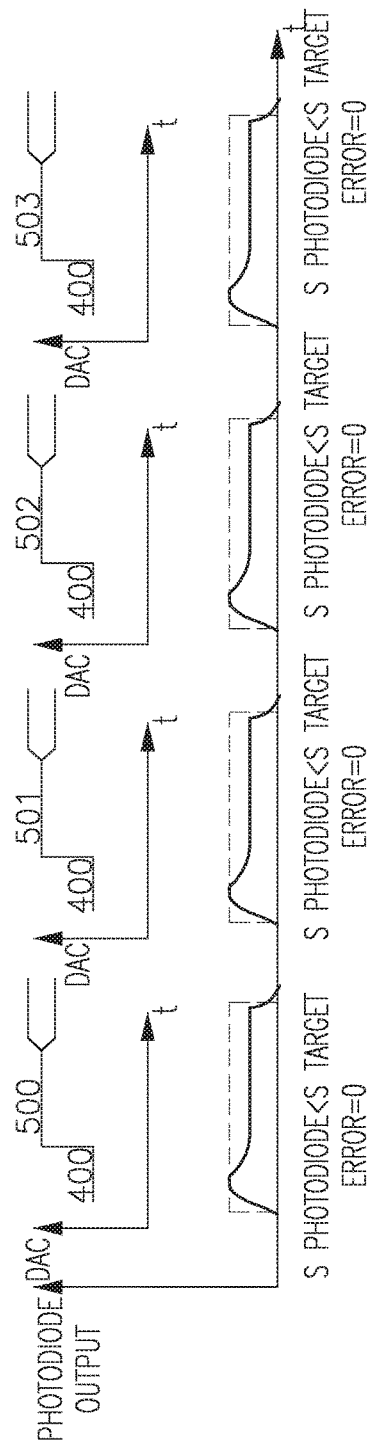
Figure 13B:
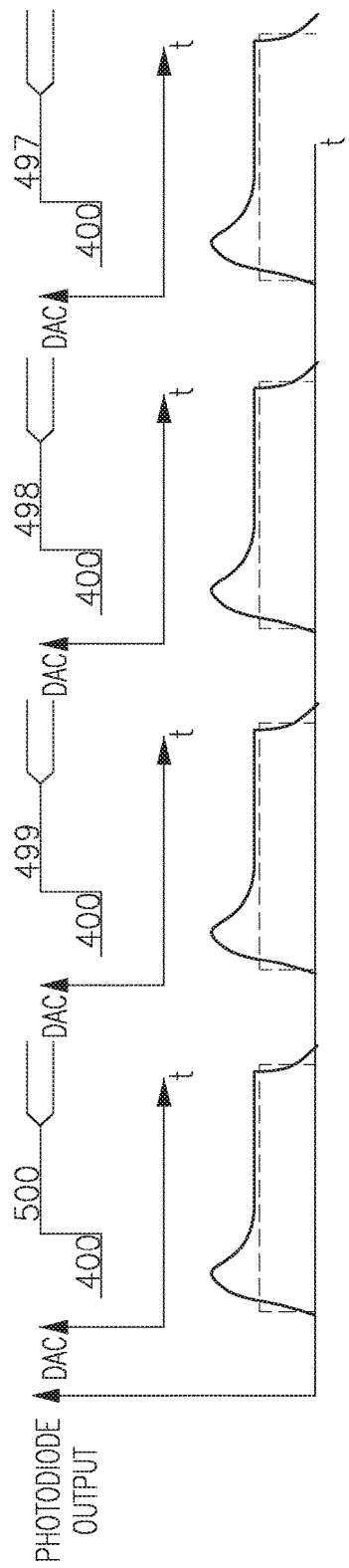

As shown in FIG. 13*a*, if the measured energy level as read from photodetector 960 is lower than the user selected energy level, FPGA 930 raises DAC value to pumping diode 940 by one DAC number. As shown in FIG. 13*b*, if the measured energy level as read from the photodetector 960 is higher than the user selected energy level, FPGA 930 reduces DAC value to pumping diode 940 be one DAC number.

Figure 14:
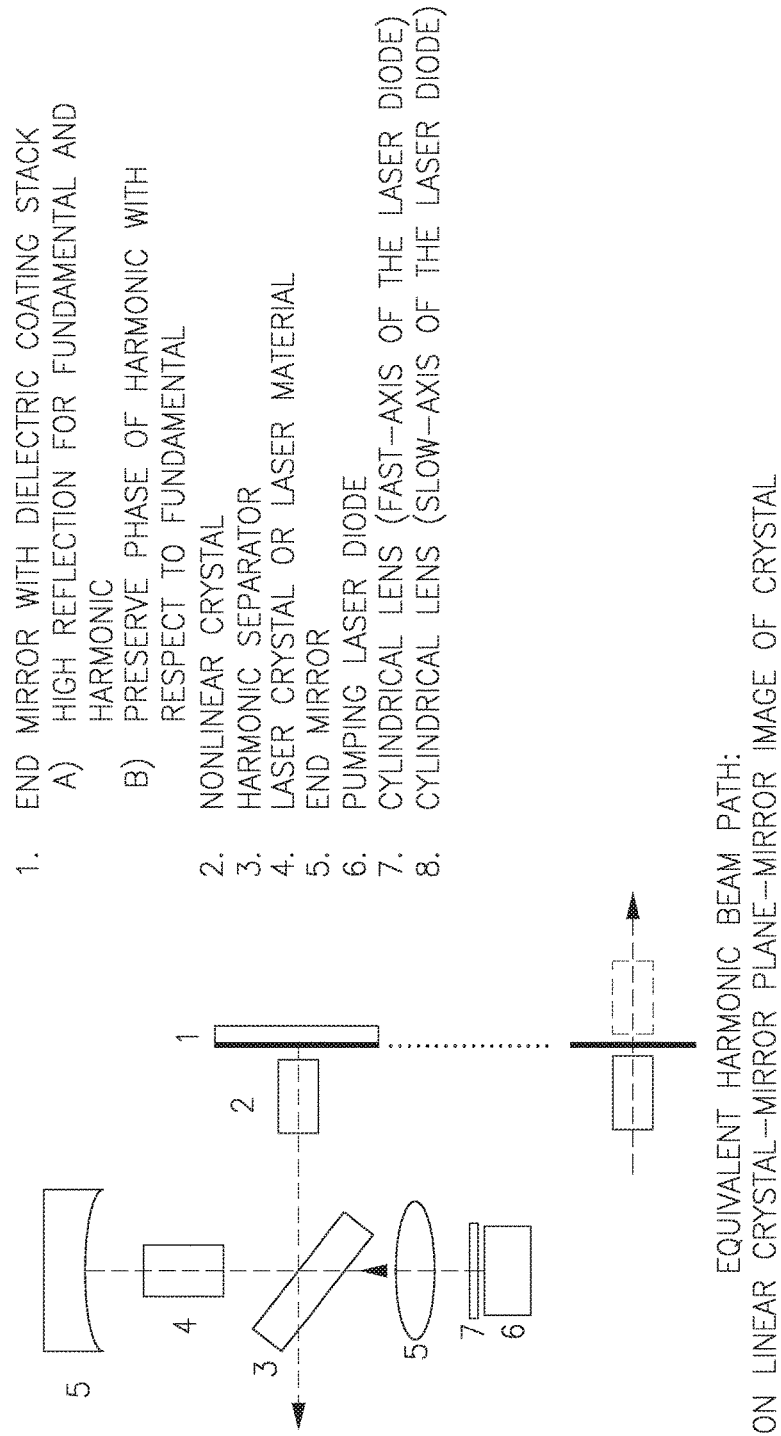

According to another aspect of the invention and referring now to FIG. 14, when pumped, gain in the laser material [4] creates an optical standing wave oscillation bounded by the mirrors [1, 3, 5] at the fundamental wavelength. The standing wave can be decomposed as the sum of two traveling waves which propagate in opposite directions. Due to the property of nonlinear polarization inside the nonlinear crystal [2], a harmonic wave may be generated, and the power of the fundamental may be transferred efficiently into the harmonic wave. The fundamental wave, as it travels from the harmonic separator [3], has its first opportunity to interact with the field of a harmonic wave as it passes through the nonlinear crystal [2] the first time. After reflection at the end mirror [1], the fundamental wave has a second opportunity to interact with the field of the harmonic wave as it passes through the nonlinear crystal the second time. When the fundamental next passes the harmonic separator, the harmonic is removed from the laser resonator and moved into the output. The system of FIG. 15 also includes a pumping laser diode [6], and cylindrical lenses [7] and [8].

The rate of flow of energy from the fundamental to the harmonic depends on the magnitude of the nonlinearly and the magnitude of the field of the fundamental. The flow of energy also depends on the matching of the phase of the fundamental to the phase of the harmonic throughout the length of the interaction. Phase mismatching inside the nonlinear crystal is described by $\Delta k = k_2 - 2k_1$, where k1 is the wavenumber of the fundamental wave and k2 is the wavenumber of the harmonic wave, considering the refractive indices of the nonlinear material. In order to achieve efficient frequency conversion, the nonlinear crystal is designed by some means to achieve a value of $\Delta k$ close to 0, so that transfer of power can occur throughout a long enough interaction length, or, in the best case, across the entire length of the nonlinear crystal. For large $\Delta k$, the harmonic wave will become out of phase with the fundamental wave, until the flow of power is reversed and the fundamental is regenerated.

For a standing wave laser, the phase difference on reflection of the end mirror [1], defined as $\varphi_2 - 2\varphi_1$, where $\varphi_1$ is the reflected phase of the fundamental and $\varphi_2$ is the reflected phase of the harmonic, is also important for efficient harmonic generation. In the worst case if $\Delta k = 0$, but $\varphi_2 - 2\varphi_1 = 180°$, then the harmonic will build power during the first pass through the nonlinear crystal. But then during the second pass after reflection, the two fields will be out of phase, so that all the harmonic power will return to the fundamental and the harmonic output will be zero. In order to achieve the optimal case where the power is continuously transferred toward the harmonic throughout the length of the crystal in two passes, the phase difference on reflection should be minimized $\varphi_2 - 2\varphi_1 \approx 0$, and also the phase mismatch should be minimized $\Delta k \approx 0$.

Even in the case in which the end mirror [1] is created by accident where $\varphi_2 - 2\varphi_1 = 180°$, the laser can still be operated by adjusting away from $\Delta k = 0$, for example by adjusting the temperature of the nonlinear crystal. In this case the harmonic output will not be as high as the case where $\varphi_2 - 2\varphi_1 = 0°$ and $\Delta k = 0$, but it will be greater than zero.

FIG. 15 illustrates an experiment in which a temperature sweep on an LBO crystal is used to sweep across a wide range of values of $\Delta k$, in this example $\Delta k = 0$ occurs at approximately 41° C. In this experiment, a wedged glass component is placed in between the laser crystal and the end mirror. The glass component has dispersion, and because of its wedge it can be used to adjust the effective of phase difference on reflection $\varphi_2 - 2\varphi_1$. Each line in the chart therefore belongs to a distinct value of $\varphi_2 - 2\varphi_1$. This illustrates that even though a solution exists for efficient harmonic generation for every value of $\varphi_2 - 2\varphi_1$, there is an optimal value of $\varphi_2 - 2\varphi_1$ for best efficiency. Theoretically we know that the optimal value must be $\varphi_2 - 2\varphi_1 = 0$.

Generally, it may be possible to increase harmonic generation efficiency by means other than control of the phase difference on reflection $\varphi_2 - 2\varphi_1$, primarily reduction of laser beam diameter, increase of the length of the nonlinear crystal, or reduction of residual losses at the fundamental, such as scattering from defects or rough surfaces. However, each of these design parameters exhibits some practical limitation. Reduction of beam diameter may be limited by laser damage limits. Eventually the reduction of residual losses becomes cost-prohibitive. The Rayleigh range of the fundamental laser beam is one limit to the length of the nonlinear crystal. The nonlinear crystal length is also inverse to the acceptance bandwidth of harmonic conversion process. If the acceptance bandwidth is reduced below the gain bandwidth of the laser material, then the laser wavelength will escape the harmonic conversion by running away at a wavelength where no conversion occurs. In this way, the gain bandwidth of the laser material defines a limit on the length of the nonlinear crystal. Longer crystal lengths can be used in this case only with the addition of some wavelength bandwidth filter inside the laser, such as an etalon or a birefringent Lyot filter.

The phase difference on reflection has been controlled in the past by using an element with adjustable chromatic dispersion, for example a glass element located in between the nonlinear crystal and the end mirror, in which the temperature of the glass is controlled and adjustable in order to achieve exactly the correct phase difference. Air also has enough dispersion that the spacing between the mirror and the nonlinear crystal can be made to be adjustable. In both cases, a random phase difference can be compensated, however these implementations suffer from additional complexity and adjustment and are often not considered worthwhile.

What we claim is:

1. A system for producing laser pulses in a microsecond scale operational mode:
the system consisting of a single loop hardware-based component;
the system further comprising:
a graphical user interface (GUI) to enable a user to select the operational mode of the system;
a laser source for producing one or more laser beam pulses, the laser source being a diode laser pump source module;
a digital signal processor (DSP) which enables and disables a hardware-based field programmable gate array (FPGA);
wherein the field programmable gate array (FPGA) controls the diode pump source module;
wherein when a user selects one or more microsecond scale laser sub-pulses on the graphical user interface (GUI), the DSP transmits to the field programmable gate array (FPGA) the sub-pulse energy level and the sub-pulse on-time selected by the user on the graphical user interface (GUI);
wherein, a photodetector operatively connected to the hardware-based system measures the power of the laser pulse beam that was transmitted to the photodetector and, in a feedback mode, transmits a feedback signal of that power measurement to the field programmable gate array (FPGA); and wherein the field programmable gate array (FPGA) compares the power of the laser beam measured by the photodetector to the power of the laser beam selected by the user on the graphical user interface (GUI);
and, wherein if power level read by the field programmable gate array (FPGA) is higher than the selected power level, the field programmable gate array (FPGA) decreases the power level to the pumping source module for any subsequent laser pulses; and if the power level read by the field programmable gate array (FPGA) is less than the selected power level, the field programmable gate array (FPGA) increases the power level to the pumping source module for subsequent laser pulses.

2. The system of claim 1, further comprising a beam splitter in the optical path of the diode laser pump source module, the beam splitter dividing a laser pulse from the laser source into two portions; one portion of the laser beam pulse being transmitted to a target tissue; the other portion of the laser beam pulse being transmitted to a photodetector.

3. The system of claim 2, wherein the beam splitter is one of a: mirror or a prism.

4. The system of claim 2, wherein the photodetector comprises more than one photodetector for redundancy operation.

5. The system of claim 1, wherein the field programmable gate array (FPGA) reads the feedback signal once every one to ten microseconds to compare measured power to selected power.

6. The system of claim 1, wherein the graphical user interface (GUI) controls the system to deliver one pulse or more than one pulse in the microsecond operational mode.

7. The system of claim 1, further comprising a calibration device to calibrate the power of one or more pulses in the microsecond scale of operation.

8. The system of claim 7, wherein the calibration device calibrates using a two-step algorithm to stabilize the energy profile of the microsecond operational mode.

9. The system of claim 8, wherein the algorithm includes a sequence of: first energy step of a set energy value, followed by a first delay period, then a second energy step of a set value followed by a second delay period.

10. The system of claim 9, wherein after the second delay, the field programmable gate array (FPGA) samples the photodetector at a specified rate of frequency in the microsecond operational mode to compare the sampled measurement from the photodetector to the selected energy level.

11. The system of claim 1, wherein a user sets on the graphical user interface (GUI) the desired pulse power level, wherein the field programmable gate array (FPGA) causes the laser module to provide one or more pulses to be measured by the photodetector to determine whether the set desired pulse level is reached; and, if so, the set power level is stored in a memory of a computer system.

12. A method for producing laser pulses with a single loop hardware-based system:
the system consisting of a single loop hardware-based device;
the method providing the single loop hardware-based system capable of producing laser pulses in a microsecond scale operational mode, the system further comprising:
a graphical user interface (GUI) to enable a user to select the operational mode of the system;
a laser source for producing one or more laser beam pulses, the laser source being a diode laser pump source module;
a digital signal processor (DSP) which enables and disables a hardware-based field programmable gate array (FPGA);
the diode pump source module being controlled by the field programmable gate array (FPGA);
wherein the method further comprises:
when a user selects one or more microsecond scale laser sub-pulses on the graphical user interface (GUI), the digital signal processor (DSP) transmits to the field programmable gate array (FPGA) the sub-pulse energy level and the sub-pulse on-time selected by the user on the GUI;
a photodetector operatively connected to the hardware-based system measuring the power of the laser pulse beam that was transmitted to the photodetector and, in a feedback mode, transmitting a feedback signal of that power measurement to the field programmable gate array (FPGA); the field programmable gate array (FPGA) comparing the power of the laser beam measured by the photodetector to the power of the laser beam selected by the user on the graphical user interface (GUI);
and, wherein if power level read by the field programmable gate array (FPGA) is higher than the selected power level, the field programmable gate array (FPGA) decreasing the power level to the pumping source module for any subsequent laser pulses; and if the power level read by the field programmable gate array (FPGA) is less than the selected power level, the field programmable gate array (FPGA) increasing the power level to the pumping source module for subsequent laser pulses.

13. The method of claim 12, further comprising the step when a user sets on the graphical user interface (GUI) the desired pulse power level, the field programmable gate array (FPGA) causes the laser module to provide one or more pulses to be measured by the photodetector to determine whether the set desired pulse level is reached; and, if so, the set power level is stored in a memory of a computer system.

14. The method of claim 12, further comprising a calibration device to calibrate the power of one or more pulses in the microsecond scale of operation.

15. The method of claim 14, wherein the calibration device calibrating using a two-step algorithm to stabilize the energy profile of the microsecond operational mode.

16. The method of claim 15, wherein the algorithm includes a sequence of: a first energy step of a set energy value, followed by a first delay period, then a second energy step of a set value followed by a second delay period.

17. The method of claim 16, further comprising the step wherein, after the second delay, the field programmable gate array (FPGA) sampling the photodetector at a high rate of frequency in the microsecond operational mode and comparing the sampled measurement from the photodetector to the selected energy level.

\* \* \* \* \*